US011612870B2

(12) United States Patent
Tang et al.

(10) Patent No.: US 11,612,870 B2
(45) Date of Patent: Mar. 28, 2023

(54) MICROENCAPSULATION OF CHEMICALS AND BIOACTIVES BY IN SITU COMPLEX COACERVATION DURING SPRAY DRYING

(71) Applicant: THE REGENTS OF THE UNIVERSITY OF CALIFORNIA, Oakland, CA (US)

(72) Inventors: Yuting Tang, Davis, CA (US); Herbert Scher, Moraga, CA (US); Tina Jeoh Zicari, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 122 days.

(21) Appl. No.: 17/178,866

(22) Filed: Feb. 18, 2021

(65) Prior Publication Data

US 2021/0316265 A1  Oct. 14, 2021

Related U.S. Application Data

(63) Continuation of application No. PCT/US2019/049591, filed on Sep. 4, 2019.
(Continued)

(51) Int. Cl.
*B01J 13/10* (2006.01)
*B01J 13/04* (2006.01)

(52) U.S. Cl.
CPC ............. *B01J 13/10* (2013.01); *B01J 13/043* (2013.01)

(58) Field of Classification Search
None
See application file for complete search history.

(56) References Cited

U.S. PATENT DOCUMENTS

2012/0309627 A1* 12/2012 Shroff .................... A01N 25/28
504/347
2014/0348815 A1* 11/2014 Jeoh-Zicari ............ B01J 13/043
536/3

FOREIGN PATENT DOCUMENTS

WO        2020051244 A1     3/2020

OTHER PUBLICATIONS

ISA/US, United States Patent and Trademark Office (USPTO), International Search Report and Written Opinion dated Nov. 19, 2019, related PCT international applicaiton No. PCT/US2019/049591, pp. 1-18, claims searched, pp. 19-25.
(Continued)

*Primary Examiner* — Jeffrey D Washville
(74) *Attorney, Agent, or Firm* — O'Banion & Ritchey LLP; John P. O'Banion

(57) ABSTRACT

An industrially scalable microcapsule, fiber or film forming process and formulations suitable for use in conventional spray drying systems are provided. The one-step spray drying process utilizes formulations of a first ionic polymer, a second ionic polymer with an isoelectric point ($pI_2$) or acid dissociation constant ($pKa_2$) that is greater than the isoelectric point ($pI_1$) or acid dissociation constant ($pKa_1$) of the first ionic polymer and a volatile base or volatile acid. Volatilization of the volatile base or acid of the spray formulation changes the pH of the solution and changes the charge of the second ionic polymer initiating electrostatic interactions with the first ionic polymer through complex coacervation. Microcapsules formed by the complex coacervation process can stabilize bioactive components as well as control the release of the bioactive components for a variety of applications.

17 Claims, 7 Drawing Sheets

Related U.S. Application Data

(60) Provisional application No. 62/727,325, filed on Sep. 5, 2018.

(56) References Cited

OTHER PUBLICATIONS

McClements, D.J. et al., "Encapsulation, Protection, and Delivery of Bioactive Proteins and Peptides Using Nanoparticle and Microparticle Systems: A Review", Advances in Colloid and Interface Science, vol. 253, pp. 1-22, Feb. 16, 2018.

Strobel, Scott A. et al., "In situ cross-linking of alginate during spray-drying to microencapsulate lipids in powder", ScienceDirect, Food Hydrocolloids 58 (2016) 141-149, published online Feb. 27, 2016.

Dubey, Rama et al., "Microencapsulation Technology and Applications", Defence Science Journal, vol. 59, No. 1, Jan. 2009, pp. 82-95.

\* cited by examiner

MICROENCAPSULATION OF CHEMICALS AND BIOACTIVES BY IN SITU COMPLEX COACERVATION DURING SPRAY DRYING

CROSS-REFERENCE TO RELATED APPLICATIONS

This application claims priority to, and is a 35 U.S.C. § 111(a) continuation of, PCT international application number PCT/US2019/049591 filed on Sep. 4, 2019, incorporated herein by reference in its entirety, which claims priority to, and the benefit of, U.S. provisional patent application Ser. No. 62/727,325 filed on Sep. 5, 2018, incorporated herein by reference in its entirety. Priority is claimed to each of the foregoing applications.

The above-referenced PCT international application was published as PCT International Publication No. WO 2020/051244 A1 on Mar. 12, 2020, which publication is incorporated herein by reference in its entirety.

STATEMENT REGARDING FEDERALLY SPONSORED RESEARCH OR DEVELOPMENT

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This technology pertains generally to microcapsules and microencapsulation methods and more particularly to an industrially scalable, single step, in situ complex coacervation microencapsulation methods and formulations.

2. Background Discussion

Microencapsulation of solid or liquid target materials has been used in many industries to isolate and protect target cores and to control release. The microencapsulation process has been used in pharmaceutical, food, chemical, cosmetic and other industries for the controlled delivery and controlled release of a wide variety of cores such as drugs, flavorings, scents, toners, inks, adhesives, paints, pesticides, fertilizers and other agricultural chemicals. Microencapsulation can provide a protective barrier, desirable release profile and compatibility with different media. It can also reduce the volatility of liquids, mask undesirable flavors and alter textures by transforming liquids to powders.

The specific target material and use may strongly influence the microencapsulation technique and the characteristics of the capsule shell that are selected. For example, desirable release kinetics for oil or water-soluble target cores can be controlled with the selection of shell materials and shell porosity. Other microcapsules must have a rigid support and be capable of being ruptured.

Complex coacervation is a particularly promising microencapsulation system. Complex Coacervation is a polymer phase separation process brought about by dissolving two ionic polymers in water at a pH where both polymers have the same charge (e.g., both are negatively charged) and then causing phase separation by dropping the pH so that one polymer maintains its negative charge, but the second polymer undergoes a charge reversal and becomes positively charged. The driving force for phase separation (complex coacervation) is electrostatic attraction.

The conventional application for microencapsulation by complex coacervation is to utilize one of the polymers (typically a protein) to emulsify a cargo compound, combine it with a second polymer (typically a polysaccharide), adjust the pH to between the pI and pKa of the polymers to encourage electrostatic interactions between the oppositely charged polymers. Following a shell-hardening incubation period, a chemical crosslinker (e.g. glutaraldehyde) is necessary to reinforce the complex coacervated matrix. Further, to obtain dry, complex coacervate microcapsules containing a target cargo, a solid/liquid separation step to recover the microcapsules followed by a drying step are necessary.

However, the potential commercial application of the conventional process is limited by the multiple steps that are required for emulsification, coacervation, shell hardening and drying. Moreover, a crosslinking step using toxic agents such as formaldehyde or glutaraldehyde is often necessary to stabilize the polymer associations, which is especially incompatible with food systems. Alternatively, use of non-toxic natural crosslinker such as genipin or an enzymatic crosslinker such as tranglutaminase has also been considered. However, no matter what type of crosslinker is used, cross linking requires precise adjustment of pH, concentrations and temperature and typically takes hours to complete. These are the primary disadvantages to the conventional encapsulation techniques and are a barrier to their use.

Microencapsulation by conventional complex coacervation is achievable at the bench-scale. However, it is challenging to scale-up to an industrial scale because of the complexity of the process. The conventional complex coacervation process through steps of pH adjustments, shell-hardening, chemical cross-linking, separation and drying is a cumbersome and resource-intensive process for microencapsulation.

Accordingly, there is a need for energy efficient, economical, and high throughput approach for microencapsulation by complex coacervation.

BRIEF SUMMARY

An industrially scalable microencapsulation process by in situ complex coacervation during spray drying (the 'CoCo process') is provided. The complexity of the conventional multistep process of pH adjustments, shell-hardening, chemical cross-linking, separation and drying remains an obstacle to commercialization. To overcome this obstacle, the conventional multistep process is collapsed into a single spray drying step to allow the formation of dry microparticles, fibers or films without the need for a chemical crosslinking agent. Spray-drying is an industrially ubiquitous unit operation; enabling complex coacervation by spray drying makes this process commercially feasible.

The preferred process delivers a mixture of two macromolecules, a cargo and a volatile base to a device that forms atomized droplets or fluid streams (e.g. spray dryer, spray coater, electrospinner and others) through which insoluble microcapsules, fibers or films are formed by complex coacervation. In one embodiment, this is accomplished by utilizing a volatile base such as ammonia to raise the pH of a spray dry feed solution to the point where both macromolecules are negatively charged, thereby preventing phase separation.

Upon atomization at the spray dry nozzle, the volatile base of the feed formulation vaporizes lowering the pH in the droplets to the point where one polymer becomes positively charged, thus allowing complex coacervation to occur as in the aqueous system. In the case of spray drying, simultaneous drying of the droplets facilitates electrostatic interactions between the oppositely charged macromolecules such that the resulting dried microparticles are insoluble.

The inclusion of active ingredients in the spray dry feed solution will result in dry cargo loaded complex coacervate microcapsules, fibers or films being produced in one process step. The simplified process incorporates the cargo into the polymer matrix (e.g. forming matrix microparticles) instead of resulting in core-shell encapsulation typical of the conventional techniques. The microcapsules produced by this process have characteristics that control the release of the cargo without the use of chemical crosslinking.

In one embodiment of the process, the emulsion is mixed with the second polymer and maintained at a pH greater than the pI and pKa of the matrix polymers using a volatile base. Optionally a non-volatile acid can be included in the spray formulation feed for tighter pH control. When the feed solution is atomized in the spray dryer, volatilization of the base decreases the pH in the droplets to between the pI and pKa of the matrix polymers. Simultaneous and rapid moisture removal facilitates polymer-polymer associations and strengthens electrostatic and van der Waals' interactions. Thus, in a single step, dry, cargo-loaded microparticles are formed without the need for additional chemical crosslinkers.

In another embodiment of the process, the cargo, first ionic polymer and the second polymer is maintained at a pH less than the pI and pKa of the matrix polymers using a volatile acid. Optionally a non-volatile base can be included in the spray formulation feed for tighter pH control. When the feed solution is atomized in the spray dryer, volatilization of the base increases the pH in the droplets to between the pI and pKa of the matrix polymers forming the capsule or particle.

This complex coacervation process produces controllable and narrowly-distributed particle sizes in the micrometer range. The CoCo process consolidates many energy-intensive, time-consuming and resource intensive steps into a single, industrially ubiquitous, energy efficient process, and reduces the toxicity of the process and product by obviating the need for chemical cross-linking.

The process is illustrated in part by forming d-limonene loaded CoCo microcapsules for evaluation. D-limonene is a bio-based volatile oil that has broad uses in food systems, eco-friendly household cleaning products, and non-fossil sourced alternate organic solvents in industrial processes, for example. Limonene is used as an illustration because the volatility and oxygen-sensitivity of limonene often limits its shelf life, stability and cost-effective use.

The microparticles produced by the CoCo process demonstrated that up to 83% of the d-limonene was retained during spray drying encapsulation, and that no significant loss of the volatile oil was found when the product was stored at room temperature for 72 days.

According to one aspect of the technology, compositions and methods are provided that enables the formation of complex coacervate microparticles, fibers or films by various spray drying processes.

Another aspect of the technology is to provide a one-step fabrication process that delivers a mixture of two macromolecules, a cargo and a volatile base to a device that forms atomized droplets or fluid streams through which insoluble microcapsules, fibers or films are formed by complex coacervation.

A further aspect of the technology is to provide a spray drying process that utilizes polymers similar to those currently used in the conventional multistep processes without the need for chemical crosslinking.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Referring more specifically to the drawings, for illustrative purposes, embodiments of a system, compositions and methods for an industrially scalable microencapsulation process by in situ complex coacervation during spray drying are generally shown. Several embodiments of the technology are described generally in FIG. 1 to FIG. 6 to illustrate the characteristics and functionality of the compositions and methods. It will be appreciated that the methods may vary as to the specific steps and sequence and the systems and apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
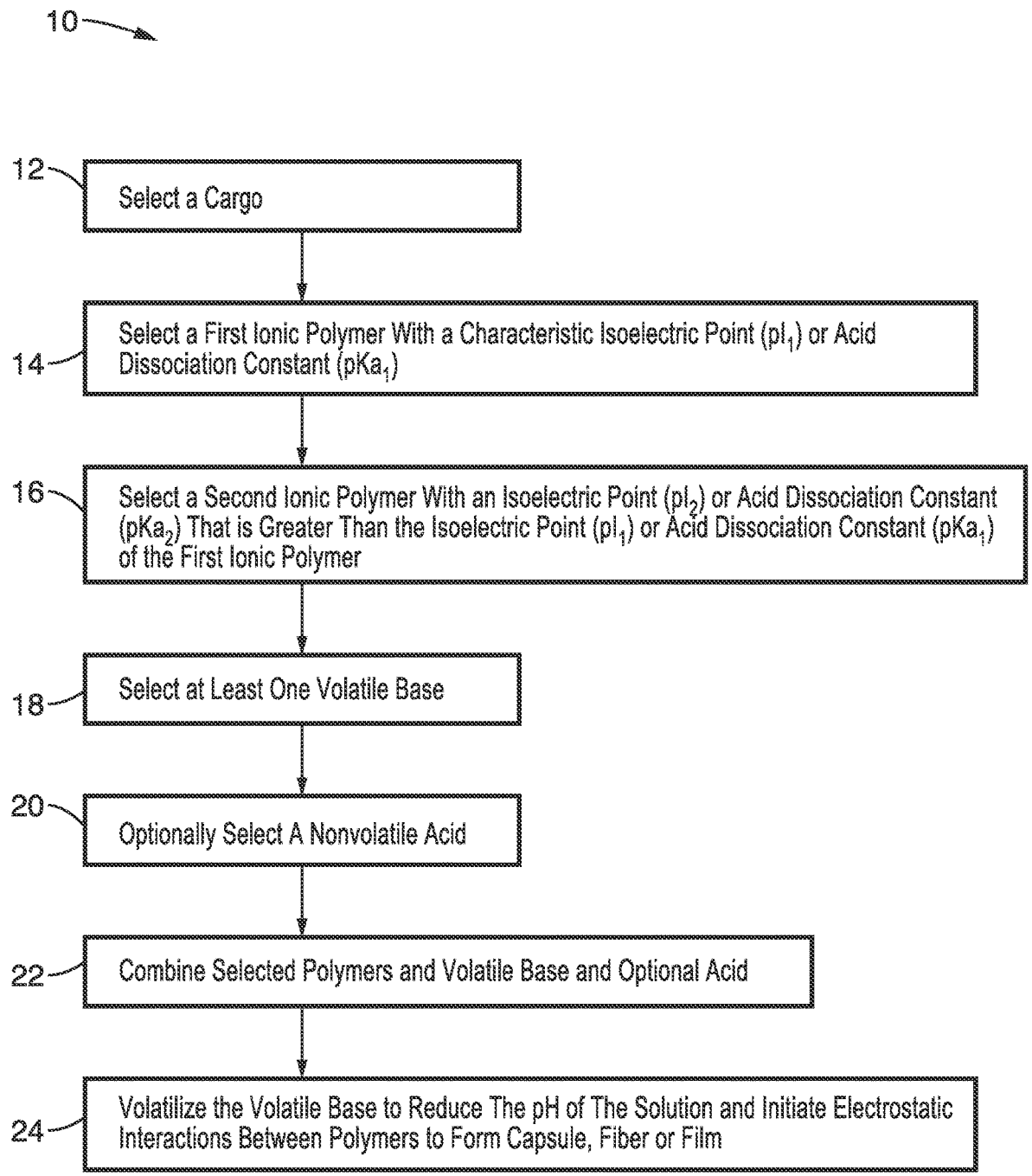
FIG. 1 is a schematic block system diagram of a method for fabricating microcapsules by complex coacervation using a volatile base according to one embodiment of the technology.

Turning now to FIG. 1, one embodiment of a method 10 for fabricating microparticles, fibers or films by complex coacervation is shown schematically and is used to illustrate the technology. In one preferred embodiment, a method of causing complex coacervation of polymer molecules is provided with the steps of: (a) providing a solution of a first ionic polymer, a second ionic polymer with an isoelectric point ($pI_2$) or acid dissociation constant ($pKa_2$) that is greater than the isoelectric point ($pI_1$) or acid dissociation constant ($pKa_1$) of the first ionic polymer and a volatile base; and then (b) volatilizing the volatile base of the solution, thereby reducing the pH of the solution and changing the charge of the second ionic polymer initiating electrostatic interactions with the first ionic polymer through complex coacervation to form a capsule, fiber, or film.

At block 12 of FIG. 1, the cargo for encapsulation is selected. The cargo that is selected can be solids or liquids and may be hydrophobic or hydrophilic materials. In some embodiments, the selection of the shell materials and other components and the quantities of components will take into consideration the nature of the cargo.

A first ionic polymer with a known isoelectric point ($pI_1$) or acid dissociation constant ($pKa_1$) is then selected at block 14 of FIG. 1. Preferred material for the first ionic polymer at block 14 is a polymer of the formulation including alginate (pKa 3.5), gum arabic (pKa 2.2), pectin (pKa 3.6), xanthan gum (pKa 2.8), carrageenan (pKa 4.3), chitosan (pKa 6.5), and polylysine (pKa 5.0).

At block 16 of FIG. 1, a second ionic polymer with an isoelectric point ($pI_2$) or acid dissociation constant ($pKa_2$) that is greater than the isoelectric point ($pI_1$) or acid dissociation constant ($pKa_1$) of the first ionic polymer is selected. Preferred materials for the second ionic polymer are ionic polymers such as type A gelatin (pI 7~9), type B gelatin (pI 4.7~5.2), whey protein (pI 5.3), chitosan (pKa 6.5) and polylysine (pKa 5.0) etc.

Different combinations of materials for the first polymer and second polymer can be used. For example, a cationic polymer and an anionic polymer can be used for the two polymers. A cationic polymer or an anionic polymer and a protein can also be paired as well and be tailored for specific applications.

Suitable volatile bases for the solution at block 18 include volatile amine bases such as ammonium hydroxide, methylamine, diethylamine, propylamine, isopropylamine, dimethylamine and isobutylamine. Although these bases are preferred, other volatile bases that are liquids at process temperatures may be used.

In one embodiment, an optional non-volatile acid is included in the formulation at block 20 that is neutralized with the volatile base for further control of pH. Suitable non-volatile acids are organic acids including malic acid, tartaric acid, oxalic acid, adipic acid, glutaric acid, citric acid, succinic acid and ascorbic acid.

At block 22, a feed mixture solution of a combination of two macromolecules, a cargo, a volatile base and optional acid is formulated. The feed formulation that is formed at block 22 may also include an optional antifoaming reagent or an optional surfactant such as gelatin, whey protein, soy protein or casein.

The preferred process delivers the formulation to a device that forms atomized droplets or fluid streams such as a spray dryer, a spray coater, an electrospinner and the like. These devices permit the volatilization of the volatile base initiating electrostatic interactions between the polymers forming the particle or film at block 24. Simultaneous removal of water facilitates tight associations between the oppositely charged polymers in this formulation.

In one preferred embodiment, the pH of an aqueous spray dry feed solution containing the selected polymers and dispersed cargo particles is adjusted to about 9.0 using ammonium hydroxide or another suitable volatile base. During the spray drying process at block 24, the pH of the spray solution is lowered sufficiently as ammonia is vaporized causing one of the polymers to change its charge from negative to positive, which initiates the electrostatically driven complex coacervation process. In addition to very substantial process simplification, the results indicate that crosslinking with aldehydes is not necessary to achieve an effective controlled release barrier as the drying process in combination with electrostatic attraction results in a very intimate polymer to polymer association which leads to a very effective controlled release barrier.

Figure 2:
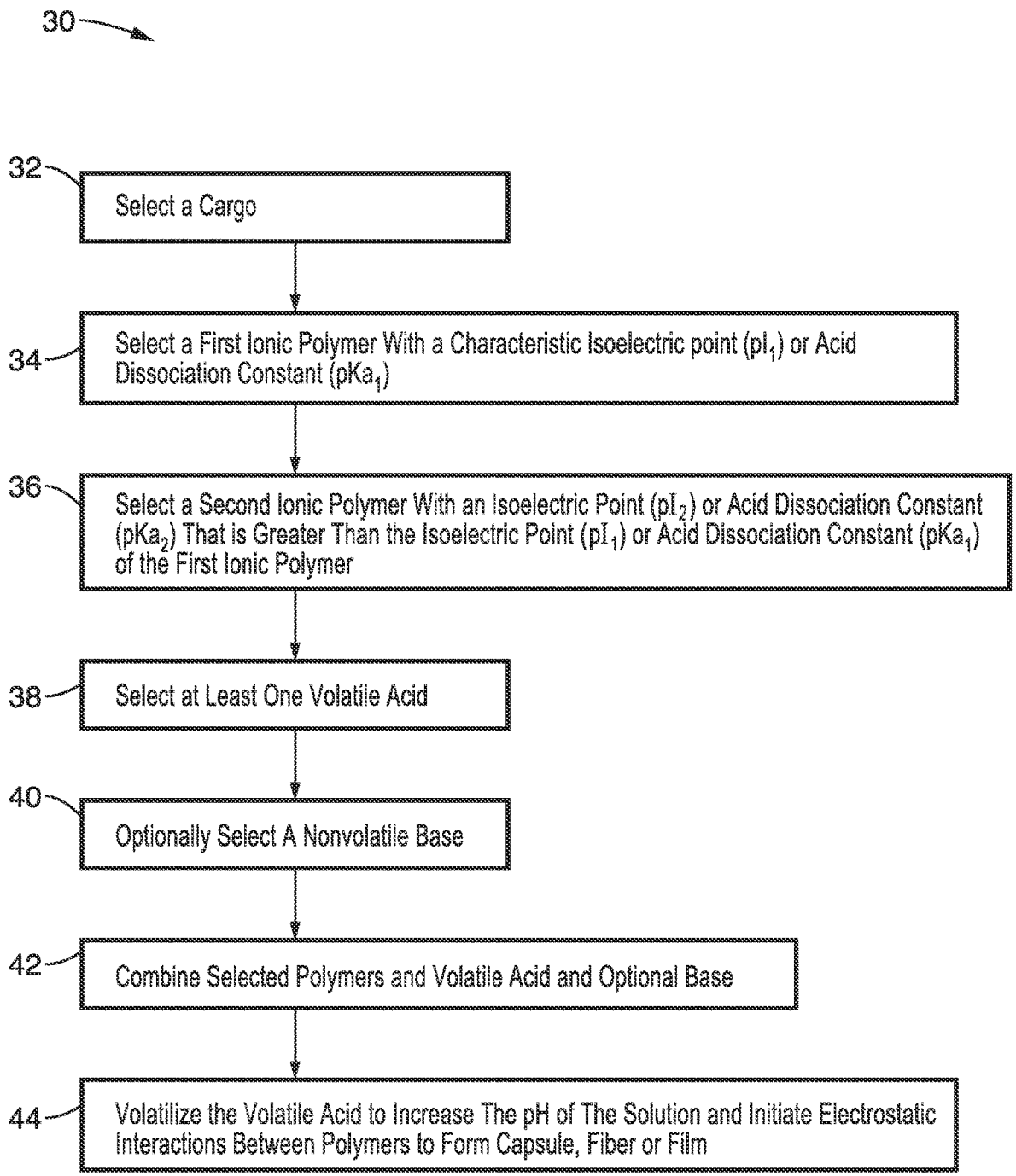
FIG. 2 is a schematic block system diagram of a method for fabricating microcapsules by complex coacervation using a volatile acid according to one embodiment of the technology.

The process may also be performed with a basic spray formulation centered on the use of a volatile acid rather than a volatile base as illustrated in FIG. 2. In one embodiment, a method 30 of causing complex coacervation of polymer molecules is provided with the steps of: (a) providing a solution of a first ionic polymer, a second ionic polymer with an isoelectric point ($pI_2$) or acid dissociation constant ($pKa_2$) that is greater than the isoelectric point ($pI_1$) or acid dissociation constant ($pKa_1$) of the first ionic polymer and a volatile acid; and (b) volatilizing the volatile acid of the solution, thereby increasing the pH of the solution and changing the charge of the first ionic polymer initiating electrostatic interactions with the second ionic polymer through complex coacervation to form a capsule, fiber, or film.

Referring now to FIG. 2, a cargo or multiple cargo materials are selected and obtained at block 32. At block 34 of FIG. 2, a first ionic polymer is selected that has a known isoelectric point ($pI_2$) or acid dissociation constant ($pKa_2$). Preferred materials for the first ionic polymer of the formulation at block 34 is a polymer from the group of alginate (pKa 3.5), pectin (pKa 3.6), xanthan gum (pKa 2.8), carrageenan (pKa 4.3), chitosan (pKa 6.5), and polylysine (pKa 5.0).

A second ionic polymer with an isoelectric point ($pI_2$) or acid dissociation constant ($pKa_2$) that is greater than the isoelectric point ($pI_1$) or acid dissociation constant ($pKa_1$) of the first ionic polymer and a volatile acid is selected and obtained at block 36.

Preferred second ionic polymers at block 36 include alginate (pKa 3.5), gum arabic (pKa 2.2), pectin (pKa 3.6), xanthan gum (pKa 2.8), carrageenan (pKa 4.3), soy protein (pI 4.6), chitosan (pKa 6.5), and polylysine (pKa 5.0).

A volatile acid is selected and obtained at the step of block 38 of FIG. 2. Suitable volatile acids in this alternative embodiment include acetic acid, formic acid, and carbonic acid.

In one embodiment, at least one optional non-volatile base is included in the formulation at block 40 that is neutralized with the volatile acid for further pH control to raise the pH for enhancement of complex coacervation during spray drying depending on the selection of ionic polymers. Preferred non-volatile bases include amines such as di-isoamylamine, diethylbenzylamine, dimethylbenzylamine, and tri-isobutylamine.

The formulation of components is prepared as a feed for a spray dryer, a spray coater, an electrospinner or other delivery device. When the feed solution is atomized in the spray dryer at block 44, volatilization of the volatile acid increases the pH in the droplets to between the pI and pKa of the matrix polymers. Simultaneously, the rapid moisture removal facilitates polymer-polymer associations and strengthens electrostatic and van der Waals' interactions. The increased pH from volatilization of the volatile acid changes the charge of the second ionic polymer initiating electrostatic interactions with the first ionic polymer through complex coacervation to form a capsule, fiber, or film.

With either embodiment, the volatilization of the volatile base or volatile acid will change the pH of the solution and change the charge of the first ionic polymer initiating the electrostatic interactions with the second ionic polymer through complex coacervation to form a capsule, fiber, or film.

Accordingly, the rate of change of pH in the solution can be controlled through control over the vaporization temperatures of the volatile acid or volatile base at block 24 or block 44. Furthermore, the degree of complex coacervation at block 24 of block 44 can be controlled by modulating one or more of the following: first and second ionic polymer concentrations or compositions, volatile or non-volatile acid concentration or composition of the solution; or the volatile or non-volatile base concentration or composition of the solution.

Figure 3A:
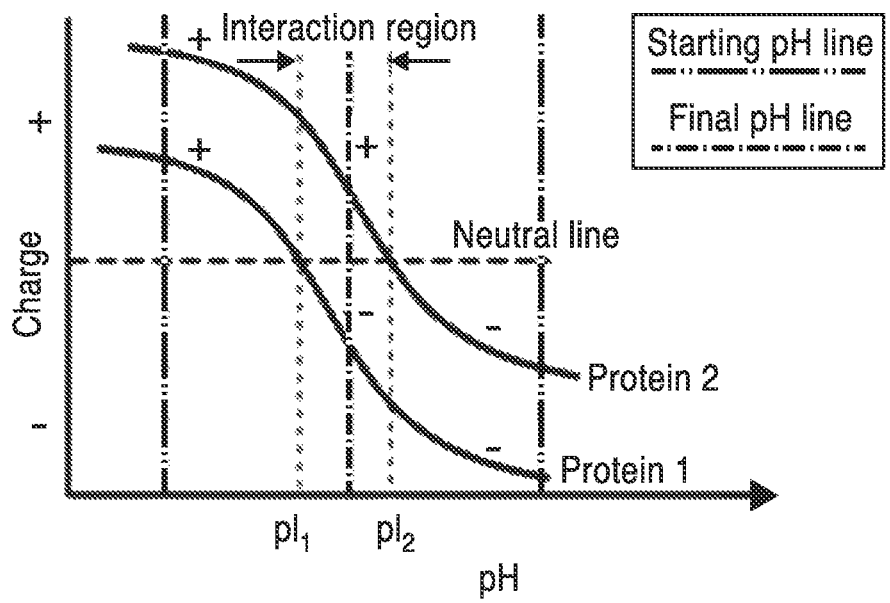
FIG. 3A is a graph of change with increasing pH and interaction zone with a formulation of two different proteins.
Figure 3B:
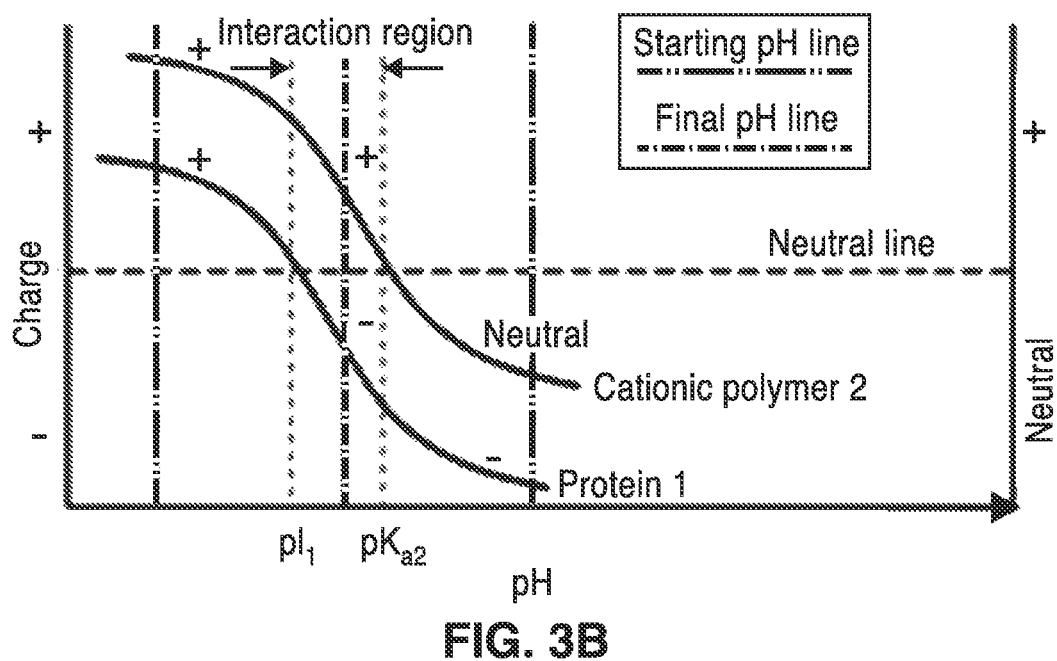
FIG. 3B is a graph of change with increasing pH and interaction zone with a formulation of a protein and a cationic polymer.
Figure 3C:
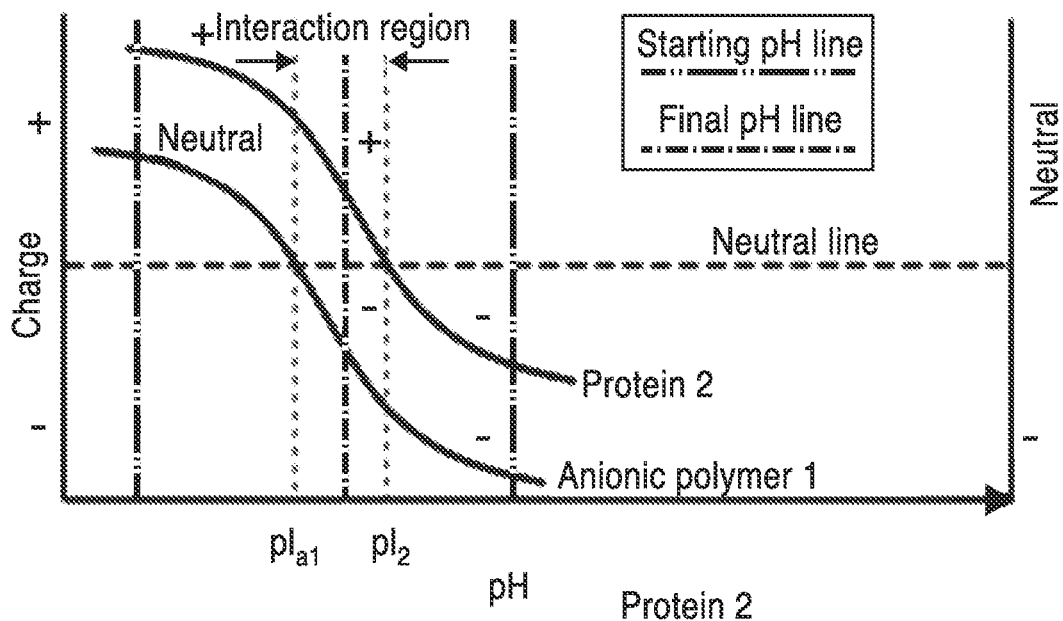
FIG. 3C is a graph of change with increasing pH and interaction zone with a formulation of an anionic polymer and a protein.
Figure 3D:
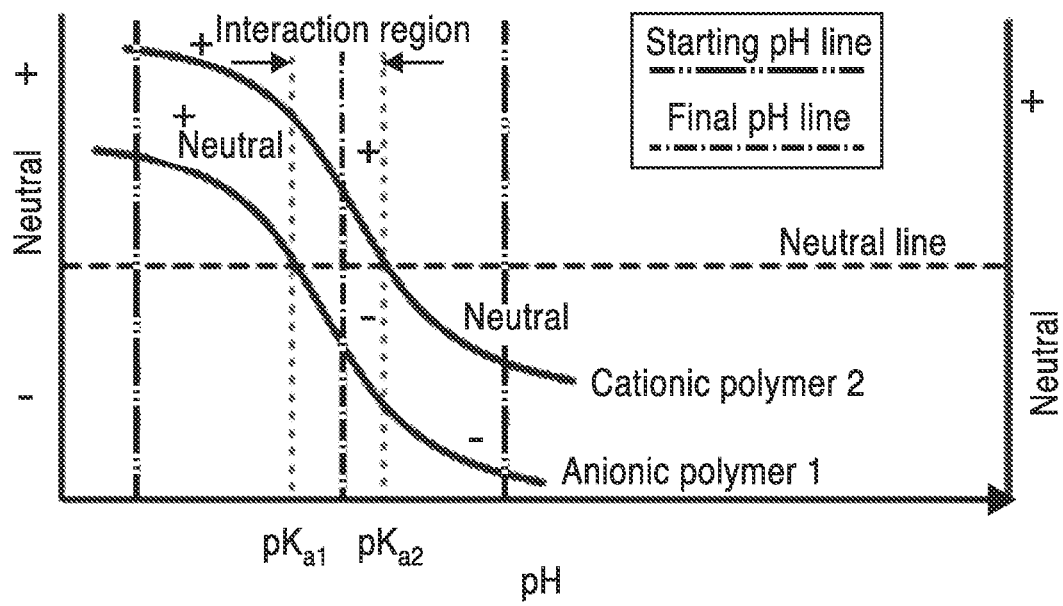
FIG. 3D is a graph of change with increasing pH and interaction zone with formulation of an anionic polymer and a cationic polymer.

The selection of polymers and their interactions by controlling the pH is illustrated in FIG. 3A through FIG. 3D. FIG. 3A through FIG. 3D demonstrate the diverse set of polymers that can be utilized to accomplish complex coacervation via evaporation of either a volatile base or a volatile acid to drive pH into the electrostatic interaction zone. In the graph of FIG. 3A, the range of pH values that will create the electrostatic interactions between a Protein 1 and a Protein 2 is shown. The two proteins, pH targets and volatile bases or volatile acids can be selected so the desired interactions take place in the interaction region of the graph. The interaction zone available with the use of a protein and a cationic polymer formulation is shown in the graph of FIG. 3B. An anionic polymer and a protein interaction zone are illustrated in the graph of FIG. 3C and the use of an anionic polymer and a cationic polymer is illustrated in FIG. 3D. The selection of an anionic polymer, cationic polymer and proteins and pH interaction zone can be assisted with the use of such graphs.

Figure 4:
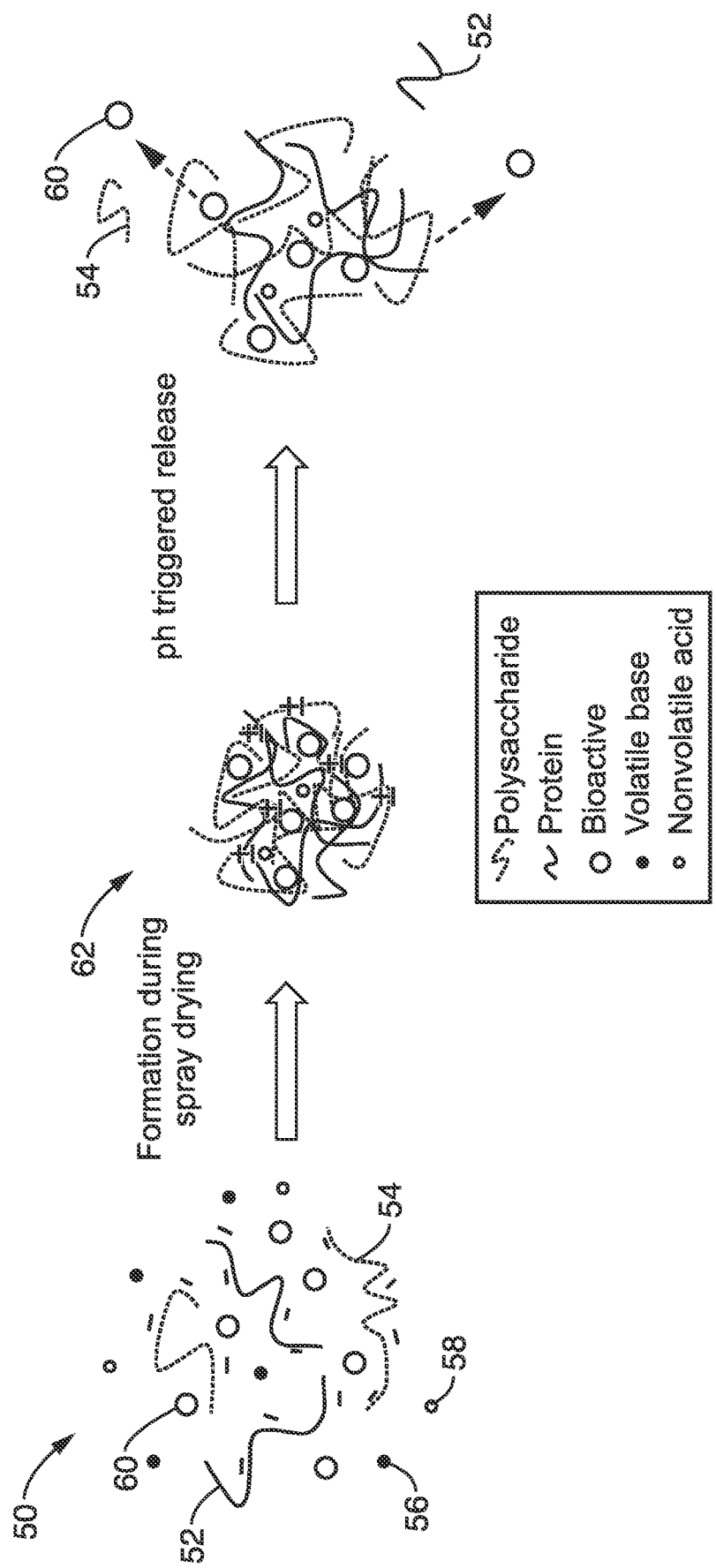
FIG. 4 is a schematic process diagram of in situ complex coacervation microencapsulation by spray drying and pH triggered release of cargo according to one embodiment of the technology.

As the formation of complex coacervates is based on the electrostatic interaction between polymers, the release of the cargo is also pH sensitive. As shown in FIG. 4, the feed formulation 50 of a first polymer (e.g. a protein) 52 and second polymer 54 (e.g. a polysaccharide), a volatile base 56 (e.g. ammonium hydroxide), a nonvolatile acid 58 (e.g. succinic acid) and bioactive 60 form particles 62 through spray drying.

The release of the bioactive cargo 60 can be controlled with a change in the pH of the environment of the particle 62 diminishing the electrostatic interactions between the first polymers 52 and the second polymers 54 releasing the cargo 60 as illustrated in FIG. 4. Control over the pH will control the rate of release of the cargo 60 from the particle 62. Overall, the matrix microcapsules formed by this industrially scalable process have the capability of stabilizing bioactive components and control the release of the bioactive components for various applications.

In addition to emulsion size, there are many other factors that may affect the retention of volatile compounds and the stability of encapsulated compounds. The volatile retention could be further increased by the modification of wall material formulation, the concentration and type of acid in the formulation, and the spray drying parameters. The pH during spray drying can be modulated to maximize the extent of complex coacervation between polymers that may lead to a tighter matrix to prevent the loss of volatiles. Furthermore, the spray drying operation parameters including the inlet air temperature, aspirator airflow rate, feed flow rate and nozzle pressure will also affect the extent of complex coacervation by influencing the ammonia loss during spray drying and residual water level in the microcapsules. The greater the water loss during spray drying, the closer the spacing between the oppositely charged polymer molecules and hence stronger the electrostatic attractive forces. The van der Waals attractive dispersion forces will also come into play as the polymer intermolecular spacing is reduced. Hence the extent of the pH lowering, and the extent of water loss will determine the insolubility of the complex coacervate polymers and the extent of complex coacervation.

The technology described herein may be better understood with reference to the accompanying examples, which are intended for purposes of illustration only and should not be construed as in any sense limiting the scope of the technology described herein as defined in the claims appended hereto.

Example 1

To demonstrate the functionality of the in situ complex coacervation during spray drying methods without cargo, formulations with a volatile base and non-volatile base and optional acid and associated yields were evaluated. Gelatin (type A, G6144) with isoelectric point (pI) equal to 7 and high viscosity sodium alginate, GRINDSTED Alginate FD 155, with a pKa of 3.5 (Dupont Nutrition and Health) were used as wall materials to form the particle matrix. The formulations used either a non-volatile base (sodium hydroxide) or a volatile base (ammonium hydroxide) or a combination of volatile base (ammonium hydroxide) and a non-volatile acid (succinic acid) in the formulation to adjust the solution pH to about 8.5.

In one trial, a solution of about 2.5% (w/w) gelatin and about 0.5% (w/w) alginate was spray dried. In one embodiment, sodium hydroxide (NaOH) was used to adjust the solution pH to about 8.5. In another trial, ammonium hydroxide ($NH_4OH$) was used to adjust the solution pH to about 8.5. In order to obtain a lower spray drying pH, a solution of about 2.5% (w/w) gelatin, 0.5% (w/w) alginate, ammonium hydroxide ($NH_4OH$) and 1% (w/w) succinic acid was spray dried and evaluated. The formulations that were used are shown in Table 1.

The prepared aqueous spray feed solution was promptly pumped into a Buchi B290 laboratory spray-dryer (New Castle, Del.) to produce dry microcapsules. The spray-drying process had operating conditions of an inlet air temperature of about 150° C., an aspirator airflow rate at about maximum (about 35 $m^3/h$), and a feed peristaltic pump at about 20% of maximum (about 6 ml/min), and 40 mm nozzle pressure.

The 'Extent of Complex Coacervation', a metric to assess the extent to which all polymers within the particles participate in complex coacervation, was defined as the fraction of polymers that do not solubilize from the CoCo particles when the spray dried powders are suspended in water. The gelatin concentration in the supernatants was measured by the Bio-Rad protein assay (Bio-Rad, Hercules, Calif.) based on the Bradford dye-binding method following manufacturer recommended protocols for the microplate microassay. The alginate concentration in the supernatants was determined using the Anthrone assay.

Successful complex coacervation during spray drying relies on sufficient decrease in the droplet pH to between the pKa of the alginate and pI of gelatin to induce electrostatic interactions. The process is designed to prevent complex coacervation prior to spray drying by maintaining a pH higher than the pKa and pI of the matrix polymers (e.g. pKa of alginate is 3.5 and pI of gelatin is 7). The role of pH drop that occurs during spray drying on the formation of complex coacervates was tested with the three formulations set forth in Table 1.

In the first formulation, a non-volatile base, sodium hydroxide, was used as a control. The second and third formulations used a volatile base, ammonium hydroxide, to lower the pH during spray drying. Succinic acid was added in the third formulation to further lower the pH during spray drying.

Spray dried powders from the three formulations were suspended in water to visually assess their solubility. The pH of each of the supernatants from the suspensions are given in Table 1. As expected, the powder prepared with sodium hydroxide (formulation 1) fully dissolved in water, indicating no complex coacervation in these particles. The powders prepared using the volatile ammonium hydroxide (formulation 2), however, remained partially undissolved in water with a supernatant pH of 5.1. When ammonium hydroxide and succinic acid were combined (formulation 3), the powder remained mostly undissolved with a supernatant pH of 4.3. These results indicate that volatilization of ammonia reduced the pH to facilitate some complex coacervation in the powder; the additional presence of succinic acid enhanced complex coacervation by driving the pH to its $pK_a$ of ~4, which is about 3 log units below the pI of gelatin.

To quantify the extent of complex coacervation, the extent to which gelatin and alginates remained undissolved from each of the three formulations of Table 1 suspended in water were measured. The spray-dried powders formulated with sodium hydroxide (formulation 1) had no insoluble gelatin or alginate, thus confirming visual observations that the powder fully dissolved, and no complex coacervation was achieved in these particles.

The partially soluble powder of formulation 2 prepared with ammonium hydroxide had 6% and 24% undissolved gelatin and alginate, respectively. Finally, the largely water insoluble powder prepared with ammonium hydroxide+succinic acid (formulation 3) had 72% and 39% undissolved gelatin and alginate, respectively.

The extent of complex coacervation was thus defined as the ratio of the undissolved gelatin and alginate to the amount of total polymer in the spray-dried complex coacervate (CoCo) samples. By this definition, the extents of complex coacervation were 0±0%, 9±2% and 65±6% for CoCo powders formulated with sodium hydroxide, ammonium hydroxide, and ammonium hydroxide+succinic acid, respectively for each of the formulations indicated in Table 1.

The results demonstrated that the one-step CoCo process successfully forms complex coacervates during spray drying. Further, the extent of complex coacervation can be modulated by the pH during spray drying, which can be controlled by the selection of base and acid in the formulation. Electrostatic interactions, considered to be the dominant interaction for complex coacervation, is strongly dependent on the charge density of the polymers (which is highly influenced by the pH) and the degree of dehydration (which controls spacing between oppositely charged sites on the polymers). Further, pH not only affects charge density but can also induce structural transitions of the polymers. Thus, in the CoCo process, the type and concentration of acid in the feed, and the resulting pH of the feed modulated by ammonium hydroxide could affect the protein structure thus the extent of complex coacervation.

Example 2

Capsule formation by in situ complex coacervation during spray drying methods without cargo was also demonstrated using several additional starting formulations. Dry powder yields and particle diameters and surface topography were also evaluated.

Spray feed formulations with a volatile base and non-volatile base and optional acid and associated yields were evaluated. In one group, the formulations used either a volatile base (ammonium hydroxide) or a non-volatile base (sodium hydroxide) in the formulation to adjust the solution pH to about 9.0. Formulations with and without the additional acid (about 1% (w/w) succinic acid) to further lower the spray dried pH were evaluated. Both types of formulations used ammonium hydroxide to adjust the solution pH to about 9.0.

In one trial, a feed of an aqueous solution was prepared with about 1.7% (w/w) of a gelation aqueous solution, about 0.44% of an alginate aqueous solution and about 0.023% ammonium hydroxide to raise the pH of the feed to about 9.2. Alginate with a pKa of about 3.5 and type A gelatin with pI of about 7.5 are both negatively charged in the feed aqueous solution.

In another trial, a solution of about 3.6% (w/w) gelatin and about 0.36% (w/w) Sigma low-viscosity alginate was spray dried. In one formulation, ammonium hydroxide ($NH_4OH$) was used to adjust the solution pH to about 9.0. In another formulation, sodium hydroxide (NaOH) was used to adjust the solution pH to about 9.0. In order to obtain a lower spray drying pH, a solution of about 2.5% (w/w) gelatin, about 1% (w/w) Sigma low viscosity alginate, ammonium hydroxide ($NH_4OH$) and about 1 (w/w) succinic acid was spray dried and evaluated.

The prepared solutions were spray dried by a Buchi B290 laboratory spray drier separately. The spray drying conditions were set at an inlet air temperature at about 150° C., aspirator airflow rate at about maximum (about 35 $m^3/h$), feed peristaltic pump at about 20% of maximum (about 6 mL/min), and 40 mm nozzle pressure. The spray dried powders were collected in glass vials and stored in a desiccator.

The yields produced by the various solutions were also compared. The yields of dry powder were about 50.0% and about 74.0% for the spray-dried powders prepared by adding ammonium hydroxide and sodium hydroxide, respectively. The observed high pH and complete dissolution of gelatin in the formulation with sodium hydroxide indicated the formation of complex coacervate microparticles by spray drying in the formulation with the volatile base (ammonium hydroxide) but not with the non-volatile base (sodium hydroxide).

The coacervated microparticles created during spray-drying have the potential to provide protection for chemicals and bioactives. In addition, the formed microparticles offer a controllable release profile due to the pH-dependent attractive forces between macromolecules. These particles have been shown to remain intact in acidic environments and dissolve in basic environments, enabling enteric release of the cargo.

Example 3

To further demonstrate the potential of the industrially-scalable complex coacervation process, the process to encapsulate d-limonene, a volatile oil. A combination of protein and polysaccharide, gelatin and alginate, was used as matrix polymers. D-limonene is a monocyclic monoterpene with a pleasant citrus-like smell and many bioactivities such as antifungal, bacteriostatic and bactericidal properties, making it appealing in many industries.

Microencapsulation can facilitate broad application of limonene by preventing volatile loss and degradation during processing and storage and by enabling controlled release of the oil.

Figure 5:
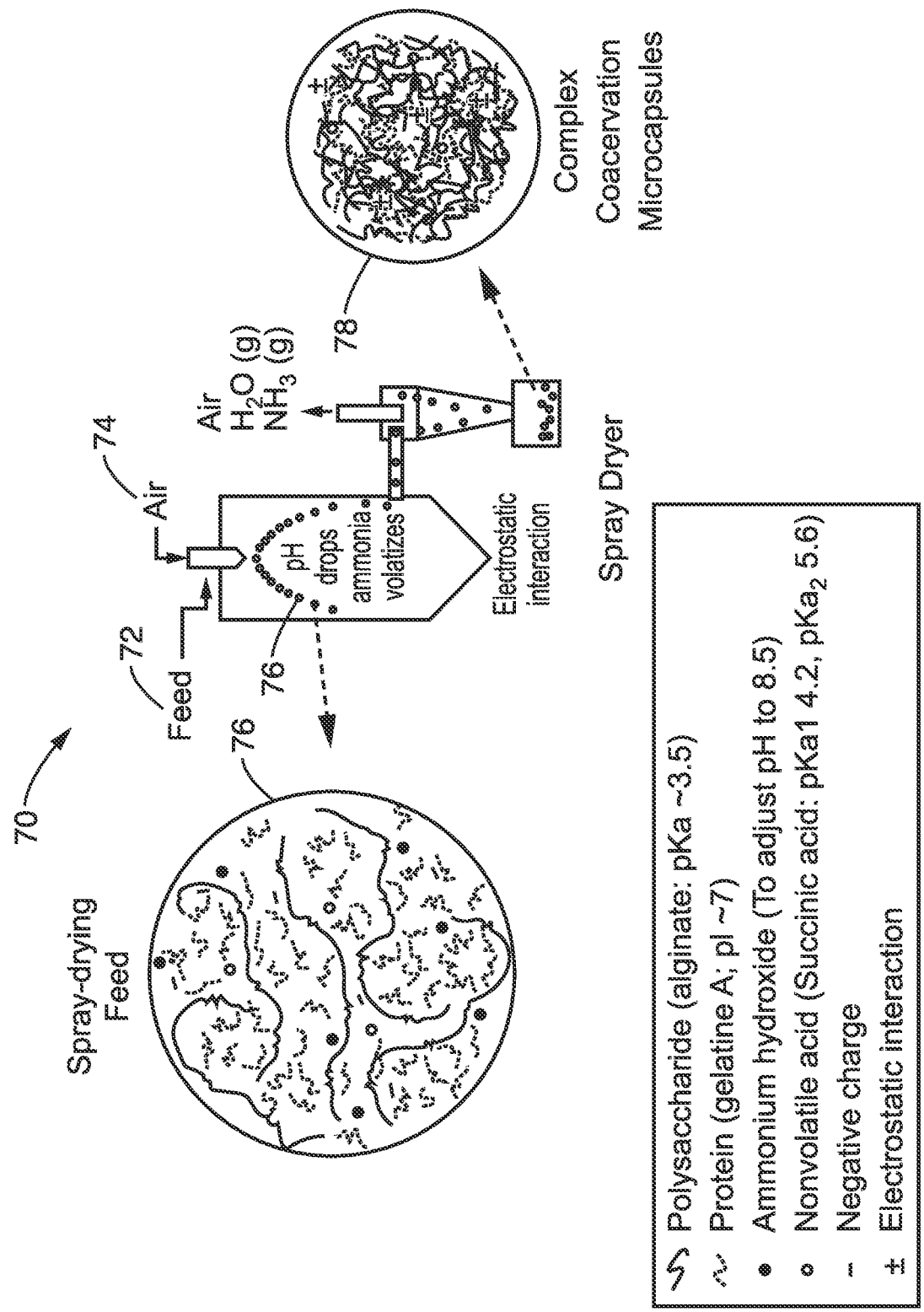
FIG. 5 is a schematic spray drying system, feed droplet and complex according to one embodiment of the presented technology.

The microencapsulation of d-limonene in CoCo microcapsules by spray drying is represented schematically in FIG. 5. The spray drying apparatus 70 has a nozzle with a formulation feed 72 and air feed 74 that produced droplets 76 within the dryer. The droplets are dried, and the volatile base volatilizes to facilitate electrostatic interactions and produce microcapsules in the embodiment illustrated in FIG. 5.

Gelatin (type A, G6144) with isoelectric point (pI) equal to 7, d-limonene, and high viscosity sodium alginate, GRINDSTED Alginate FD 155, with a pKa of 3.5 (Dupont Nutrition and Health) were used.

Limonene emulsions (5.71% (w/w)) were prepared with 5:1 d-limonene to gelatin ratio. Three emulsification processes were examined: 1) coarse emulsification using an Ultra-Turrax T-18 (IKA Works, Inc., Wilmington, Del.) only; 2) course emulsification followed by high pressure homogenization (BEEi Nano DeBEE 30-4, BEE international, South Easton, Mass.) with 2 passes and cooling using iced-water; and 3) coarse emulsification followed by high pressure homogenization with four passes and cooling using room temperature water.

To form limonene-loaded complex coacervates (L-CoCo), the emulsion was mixed with a solution containing gelatin, alginate, succinic acid and ammonium hydroxide at pH 8.5. The final target feed composition in the spray drying feed 72 was 2.5% (w/w) gelatin, 0.5% (w/w) alginate, 1.33% (w/w) limonene, and 1% (w/w) succinic acid. Ammonium hydroxide was used to adjust the spray drying feed pH to 8.5. The feed was spray dried by a Buchi B290 laboratory spray dryer at an inlet air temperature of 150° C., maximum aspirator airflow rate (35 m$^3$/h), 20% of maximum feed peristaltic pump flow rate (6 ml/min), and 40 mm nozzle pressure. The outlet temperature was 87° C. to 92° C. during spray drying.

The effectiveness of the microencapsulation process for volatile cargo was evaluated by determining the volatile retention of d-limonene during spray drying and storage. Volatile retention (VR) was calculated as the ratio of the amount of limonene that exits the spray dryer in the dry particles to the amount of limonene that enters the spray dryer with the feed.

An emulsion of d-limonene was microencapsulated in gelatin and alginate using ammonium hydroxide and succinic acid to control the pH during spray drying to form the limonene-loaded complex coacervation microcapsules (L-CoCo). The spray dryer in-feed was formulated to target 25% dry basis d-limonene loading in L-CoCo; however, approximately 20% of d-limonene was lost during preparation of the feed as seen in Table 2. Compared to the limonene content in the feed, the volatile retention of d-limonene in L-CoCo during spray drying was 82.7±3.6%. As expected, the L-CoCo surfaces had minimal d-limonene (0.24±0.0%). The extent of complex coacervation in L-CoCo was 75±6% (Table 1). The limonene cargo had no significant effect on the extent of complex coacervation.

Industrial spray drying is a continuous process such that the spray dried powders are removed from the collection chamber immediately, with minimal incubation time spent at outlet conditions. In contrast, in the bench-scale batch spray dryer used in the current study, spray-dried powders remain in the collection chamber at the elevated outlet temperature (87 to 92° C.) for the duration of the batch process. The extended exposure of the L-CoCo powder to the higher outlet temperature may result in greater losses of volatile compounds in the spray dryer. The influence of the amount of time that the L-CoCo powders spent in the collection chamber on volatile retention of d-limonene was investigated by varying the feed volumes (Table 2). Almost tripling the incubation time of L-CoCo samples in the collection chamber from 12 min to 35 min (L-CoCo and LT-L-CoCo, respectively) did not significantly impact the surface limonene content or the volatile retention of d-limonene in the powder. These results indicate that the CoCo matrix served as an effective barrier to protect the volatile cargo during extended exposure to elevated temperatures of 87 to 92° C.

The efficacy of the process on the storage of microcapsules with volatile cargo was also evaluated. The L-CoCo powders were stored in sealed vials in a desiccator at room temperature. After 72 days of storage, the retention of d-limonene in the LS-L-CoCo powder saw no significant loss, with the volatile retention at 80.0±3.3%. Extended incubation at the elevated temperatures in the collection chamber, however, appeared to accelerate loss during storage; a 10% decrease in d-limonene content was observed after 72 days on the shelf of the LT-L-CoCo samples (79.4±3.3% and 69.9±4.2% volatile retention for LT-L-CoCo and LTLS-L-CoCo, respectively). Surface d-limonene content decreased by half for all samples during the 72 days of storage. Taken together, the analysis of d-limonene retention in L-CoCo samples demonstrate that the CoCo process creates a matrix of gelatin and alginate that effectively prevents the loss of volatile cargo. The CoCo matrix formed by electrostatic interactions during spray drying provides good protection during extended exposure to elevated temperatures and is effective at retaining volatile cargo during storage.

The influence of the emulsifying process on volatile retention of limonene in L-CoCo microcapsules was also investigated. The d-limonene emulsions for the L-CoCo samples (Table 2). were prepared by a two-step process starting with coarse emulsification by a disperser, followed by high pressure homogenization. Generally, as the emulsion is subjected to high shear and cavitation during homogenization, emulsions with submicron particle sizes are generated and particle size decreases with increasing number of passes. Lower level of homogenization, achieved by decreasing the number of passes and by cooling with iced water, resulted in an unstable emulsion with larger, agglomerated emulsion droplets (69 μm mean diameter) and decreased volatile retention (~−10% compared to L-CoCo) during spray drying (LH-L-CoCo, Table 2). Eliminating high-pressure homogenization and only using a single coarse emulsification step resulted in smaller average emulsion size of 6 μm; however, significantly greater losses were incurred during emulsification and spray drying, resulting in a volatile retention during spray drying of only 42.5±2.0% and a limonene content of only 8.3±0.3% (U-L-CoCo, Table 2).

Despite the high volatile retention in the L-CoCo sample, the emulsion was unstable and formed larger aggregated droplets (15 μm, Table 2). Gelatin could denature during high pressure homogenization; moreover, circulating iced water through the product-cooling heat exchanger could exacerbate the agglomeration of denatured gelatin. In the preparation of the L-CoCo feed, the emulsion is mixed with the solution of containing gelatin, alginate, succinic acid and ammonium hydroxide, which may contribute to stabilizing the emulsion.

Example 4

The size and morphology of the CoCo microparticles was evaluated to verify the complex coacervation methods. The particle size distribution of the spray dried powders was measured at room temperature (25° C.) using propan-2-ol as a dispersant to prevent swelling. Measurements were conducted using a Mastersizer 3000 (Malvern Instrument, Westborough, Mass.) with the following parameters: material refractive and absorption indices of 1.51 and 0.1, respectively, and propan-2-ol dispersant refractive index of 1.39. Each sample was measured in triplicate. The d-limonene emulsion droplet size before spray drying was also measured in the Mastersizer at 25° C. using a limonene refractive index of 1.47 and water dispersant refractive index of 1.33. The emulsion was diluted 50-fold in water prior to the measurement. Each sample was measured in triplicate.

Morphological characterization of the particles by scanning electron microscopy (SEM) was also conducted. Spray dried complex coacervate powders were mounted on double-sided carbon tape, sputter-coated in gold, and imaged using a Hitachi S-4100 FE-SEM with an electron beam acceleration voltage of 5 kV.

SEM images of the CoCo samples showed particles ranging from approximately 1 μm to 20 μm. The general morphology of the spray dried particles resembles those of cargo-loaded calcium cross-linked alginate microcapsules (CLAMs) prepared by spray drying. No evidence of breakage or blow-holes were observed in the particles. Smaller (~1 μm) CoCo particles exhibited undulations and indentations, while larger particles had smoother surfaces.

Limonene loaded CoCo particles with high volatile retention of 82.7±3.6% (L-CoCo) and lower volatile retention of 42.5±2.0% (C-L-CoCo) appeared very similar with few features that distinguish between the two samples. Dents, wrinkles and shrinkages were observed in all the CoCo powders. A mixture of indented and smooth surfaces observed in the spray dried complex coacervation powders is common in spray dried powders as reported in many studies. The morphology of the powder particles is purported to affect the stability of encapsulated flavors, for example. L-CoCo with high volatile retention had smoother surfaces that may have contributed to preventing the loss of volatiles.

Figure 6:
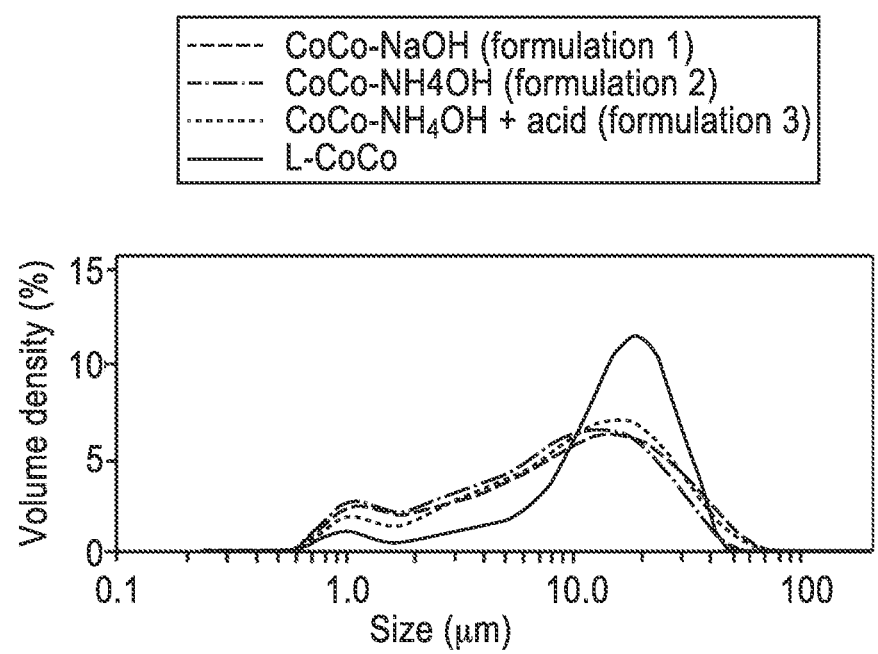
FIG. 6 is a graph of particle size distributions of spray dried CoCo microcapsules measured in isopropanol.

As shown in FIG. 6, the particle size distribution of spray dried CoCo particles generally exhibited a monomodal size distribution with a peak that is centered at about 20 μm. This was consistent with the observations from the SEM images. The volume-weighted mean diameter ($D_{4,3}$) of CoCo powder formulated with volatile base was 12.9±0.03 μm, which was the smallest among all the samples. The $D_{4,3}$, 10th percentile diameter (D(0.1)), median diameter (D(0.5)), and the 90th percentile diameter (D(0.9)) all increased with the addition of non-volatile base or acid. D-limonene loading appeared to influence the particle size distribution. The $D_{4,3}$, D(0.1), D(0.5), and D(0.9) for the L-CoCo sample were 17.9±0.07 μm, 7.25±0.01 μm, 16.8±0.3 μm and 30.2±0.1 μm, respectively.

The CoCo process allows high throughput production of microcapsules with narrow distribution of sizes. The particles formed by the CoCo process (<50 μm) are sufficiently small to be below sensory threshold, thus facilitating its application in many industries, especially the food and beverage industry.

Example 5

Limonene encapsulated complex coacervates were compared to calcium cross-linked alginate microcapsules (CLAMS). The limonene complex coacervate microcapsules were prepared with an emulsion of about 2.5% (w/w) gelatin, about 1% (w/w) Sigma alginate, about 1% (w/w) succinic acid, and limonene was spray dried. Ammonium hydroxide ($NH_4OH$) was used to adjust the solution pH to about 8.7. The target limonene loading was about 25% based on the dry inlet compositions (excluding ammonium hydroxide). Gelatin was also used as surfactant and about 0.005% (w/w) of an optional antifoam reagent was added to reduce foam during the process of making coarse emulsion (prepared by an Ultra-Turrax T-18). A coarse emulsion went into a high-pressure homogenization (BEEi Nano DeBEE 30-4 High Pressure Homogenizer) that produced a highly stable emulsion with submicron-sized oil particles. The solution was spray dried by a Buchi B290 laboratory spray drier.

For the comparison, calcium crosslinked alginate microcapsules were prepared. A suspension of about 2% (w/w) Sigma low viscosity alginate, about 1% (w/w) succinic acid adjusted to about pH 7 with ammonium hydroxide ($NH_4OH$), about 0.5% (w/w) $CaHPO_4$, limonene, and surfactant (about 0.28% (w/w) gelatin or about 0.26% (w/w) whey protein) was spray dried. The target limonene loading was about 25% based on the dry inlet suspension compositions, and the ratio of limonene to surfactant was about 5:1 (w/w). When using gelatin as a surfactant, about 0.005% (w/w) antifoam reagent was added to reduce foam during the process of making a coarse emulsion (prepared by an Ultra-Turrax T-18). The coarse emulsion went into a high-pressure homogenization (BEEi Nano DeBEE 30-4 High Pressure Homogenizer), resulting in a highly stable emulsion with submicron-sized oil particles. The suspension was then spray dried by a Buchi B290 laboratory spray drier.

Limonene extraction and analysis of both sets of microcapsules was conducted. The extraction of limonene in the emulsion was performed right after homogenization. Extractions from the surface and total limonene in complex coacervates prepared by Sigma low viscosity alginate were performed about 5 and about 3 days after spray drying, respectively. Extractions of the surface and total limonene in CLAMs using gelatin or whey protein as a surfactant were performed about 5 and about 2 days after spray drying, respectively.

Table 3 is a comparison of the VR of limonene in complex coacervation microcapsules and VR of limonene in comparable CLAMs microcapsules. The VR of limonene in the complex coacervation microcapsules was 37.02±4.71% with surface limonene content of 0.72±0.04%. The VR of limonene in CLAMs using gelatin as surfactant was about 24.54±0.79%, while the VR of limonene in CLAMs using whey protein as surfactant was about 41.03±4.84%. No surface limonene was detected in CLAMs with whey protein as the surfactant, but a small amount of limonene was detected in CLAMs with gelatin as surfactant. These results demonstrate that the complex coacervation microcapsules offers comparable retention of limonene as found in calcium cross-linked CLAMs capsules.

The CoCo process is not limited to encapsulating volatile compounds but can easily be used to microencapsulate other valuable compounds. As the formation of complex coacervation microcapsules is based on electrostatic interaction between polymers, proper selection of an amphoteric polymer with an isoelectric point and an ionic polymer with acid/base dissociation constants will generate complex coacervation microcapsules that respond differently under various pH conditions. The pH-triggered release of the cargo by complex coacervation microcapsules can be modulated by selection of polymers and the pH of the environment, thus bringing numerous benefits to facilitate their applications in different areas. This microencapsulation process can be utilized for the protection and controlled release of bioactives, cells, pesticides, food ingredients and specialty chemicals.

From the description herein, it will be appreciated that the present disclosure encompasses multiple embodiments which include, but are not limited to, the following:

1. An encapsulant or film forming composition, comprising: (a) a first ionic polymer with an isoelectric point (pI1) or an acid dissociation constant ($pKa_1$); (b) a second ionic polymer with an isoelectric point ($pI_2$) or an acid dissociation constant ($pKa_2$) that is greater than the isoelectric point ($pI_1$) or acid dissociation constant ($pKa_1$) of the first ionic polymer; and (c) at least one volatile base; (d) wherein the first ionic polymer and the second ionic polymer both have a negative charge, or the first ionic polymer has a negative charge and the second ionic polymer has a neutral charge.

2. The composition of any preceding or following embodiment: wherein the first ionic polymer is an anionic polymer; and wherein the second ionic polymer is a cationic polymer with an isoelectric point ($pI_2$) or an acid dissociation constant ($pKa_2$) that is greater than the isoelectric point ($pI_1$) of the anionic polymer or the acid dissociation constant ($pKa_1$) of the anionic polymer.

3. The composition of any preceding or following embodiment: wherein the first ionic polymer is an anionic polymer; and wherein the second ionic polymer is a protein with an isoelectric point ($pI_2$) or an acid dissociation constant ($pKa_2$) that is greater than the isoelectric point ($pI_1$) of the anionic polymer or the acid dissociation constant ($pKa_1$) of the anionic polymer.

4. The composition of any preceding or following embodiment: wherein the first ionic polymer is a protein polymer; and wherein the second ionic polymer is a cationic polymer with an isoelectric point ($pI_2$) or an acid dissociation constant ($pKa_2$) that is greater than the isoelectric point ($pI_1$) of the protein polymer or the acid dissociation constant ($pKa_1$) of the protein polymer.

5. The composition of any preceding or following embodiment, wherein the first ionic polymer is a polymer selected from the group of ionic polymers consisting of alginate (pKa 3.5), gum arabic (pKa 2.2), pectin (pKa 3.6), xanthan gum (pKa 2.8), hyaluronic acid (pKa 2.9), carrageenan (pKa 4.3), chitosan (pKa 6.5), and polylysine (pKa 5.0).

6. The composition of any preceding or following embodiment, wherein the second ionic polymer is a polymer selected from the group of ionic polymers consisting of type A gelatin (pI 7~9), type B gelatin (pI 4.7~5.2), whey protein (pI 5.3), chitosan (pKa 6.5) and polylysine (pKa 5.0).

7. The composition of any preceding or following embodiment, wherein the volatile base is ammonium hydroxide.

8. The composition of any preceding or following embodiment, wherein the volatile base is selected from the group of volatile amine bases consisting of methylamine, diethylamine, dimethylamine, propylamine, isopropylamine and isobutylamine.

9. The composition of any preceding or following embodiment, further comprising at least one non-volatile acid, the acid neutralized with the volatile base.

10. The composition of any preceding or following embodiment, wherein the acid is an organic acid selected from the group of acids consisting of malic acid, tartaric acid, oxalic acid, adipic acid, glutaric acid, citric acid, succinic acid and ascorbic acid.

11. The composition of any preceding or following embodiment, further comprising a cargo material for encapsulation.

12. The composition of any preceding or following embodiment, further comprising an antifoaming reagent.

13. The composition of any preceding or following embodiment, further comprising a surfactant.

14. The composition of any preceding or following embodiment, wherein the surfactant is a surfactant selected from the group of surfactants consisting of gelatin, whey protein, soy protein and casein.

15. An encapsulant or film forming composition, comprising: (a) a first ionic polymer with an isoelectric point ($pI_1$) or an acid dissociation constant ($pKa_1$); (b) a second ionic polymer with an isoelectric point ($pI_2$) or an acid dissociation constant ($pKa_2$) greater than the isoelectric point ($pI_1$) or acid dissociation constant ($pKa_1$) of the first ionic polymer; and (c) at least one volatile acid; (d) wherein the first polymer and the second polymer both have a positive charge, or the first polymer has a neutral charge and the second polymer has a positive charge.

16. The composition of any preceding or following embodiment: wherein the first ionic polymer is an anionic polymer; and wherein the second ionic polymer is a cationic polymer with an isoelectric point ($pI_2$) or an acid dissociation constant ($pKa_2$) that is greater than the isoelectric point ($pI_1$) of the anionic polymer or the acid dissociation constant ($pKa_1$) of the anionic polymer.

17. The composition of any preceding or following embodiment: wherein the first ionic polymer is an anionic polymer; and wherein the second ionic polymer is a protein with an isoelectric point ($pI_2$) or an acid dissociation constant ($pKa_2$) that is greater than the isoelectric point ($pI_1$) of the anionic polymer or the acid dissociation constant ($pKa_1$) of the anionic polymer.

18. The composition of any preceding or following embodiment: wherein the first ionic polymer is a protein polymer; and wherein the second ionic polymer is a cationic polymer with an isoelectric point ($pI_2$) or an acid dissociation constant ($pKa_2$) that is greater than the isoelectric point ($pI_1$) of the protein polymer or the acid dissociation constant ($pKa_1$) of the protein polymer.

19. The composition of any preceding or following embodiment, wherein the volatile acid is selected from the group of volatile acids consisting of acetic acid, formic acid, and carbonic acid.

20. The composition of any preceding or following embodiment, wherein the first ionic polymer is a polymer selected from the group of ionic polymers consisting of alginate (pKa 3.5), pectin (pKa 3.6), xanthan gum (pKa 2.8), carrageenan (pKa 4.3), chitosan (pKa 6.5), and polylysine (pKa 5.0).

21. The composition of any preceding or following embodiment, wherein the second ionic polymer is a polymer selected from the group of ionic polymers consisting of type A gelatin (pI 7~9), type B gelatin (pI 4.7~5.2), whey protein (pI 5.3), chitosan (pKa 6.5) and polylysine (pKa 5.0) etc.

22. The composition of any preceding or following embodiment, further comprising at least one non-volatile base, the base neutralized with the volatile acid.

23. The composition of any preceding or following embodiment, further comprising a cargo material for encapsulation.

24. A method of causing complex coacervation of polymer molecules, comprising: (a) providing a solution of a first ionic polymer, a second ionic polymer with an isoelectric point ($pI_2$) or acid dissociation constant ($pKa_2$) that is greater than the isoelectric point ($pI_1$) or acid dissociation constant ($pKa_1$) of the first ionic polymer and a volatile base; and (b) volatilizing the volatile base of the solution, thereby reducing the pH of the solution and changing the charge of the second ionic polymer initiating electrostatic interactions with the first ionic polymer through complex coacervation to form a capsule, fiber, or film.

25. The method of any preceding or following embodiment, further comprising adding a cargo material to the solution prior to volatilization of the volatile base.

26. The method of c any preceding or following embodiment, further comprising controlling volatile base vaporization temperatures to control the rate of change of pH in the solution.

27. The method of any preceding or following embodiment, wherein the volatile base of the solution is ammonium hydroxide.

28. The composition of any preceding or following embodiment, wherein the volatile base is selected from the group of volatile amine bases consisting of diethylamine, propylamine, isopropylamine, methylamine, dimethylamine and isobutylamine.

29. The method of any preceding or following embodiment, the solution further comprising a non-volatile acid to further lower the pH for enhancement of complex coacervation during spray drying depending on the selection of ionic polymers.

30. The composition of any preceding or following embodiment, wherein the acid is an organic acid selected from the group of acids consisting of malic acid, tartaric acid, oxalic acid, adipic acid, glutaric acid, citric acid, succinic acid and ascorbic acid.

31. The method of any preceding or following embodiment, further comprising controlling a degree of complex coacervation by modulating one or more of the following: first and second ionic polymer concentrations, volatile or non-volatile acid concentration of the solution or volatile or non-volatile base concentration of the solution.

32. A method of causing complex coacervation of polymer molecules, comprising: (a) providing a solution of a first ionic polymer, a second ionic polymer with an isoelectric point ($pI_2$) or acid dissociation constant ($pKa_2$) that is greater than the isoelectric point (pI1) or acid dissociation constant ($pKa_1$) of the first ionic polymer and a volatile acid; and (b) volatilizing the volatile acid of the solution, thereby increasing the pH of the solution and changing the charge of the first ionic polymer initiating electrostatic interactions with the second ionic polymer through complex coacervation to form a capsule, fiber, or film.

33. The method of any preceding or following embodiment, further comprising adding a cargo material to the solution prior to volatilization of the volatile acid.

34. The method of any preceding or following embodiment, further comprising controlling volatile acid vaporization temperatures to control the rate of change of pH in the solution.

35. The method of any preceding or following embodiment, wherein the volatile acid of the solution is selected from the group of volatile acids consisting of acetic acid, formic acid, and carbonic acid.

36. The method of any preceding or following embodiment, the solution further comprising a non-volatile base to further increase the pH for enhancement of complex coacervation during spray drying depending on the selection of ionic polymers.

37. The method of any preceding or following embodiment, wherein the non-volatile amine is selected from the group of non-volatile amines consisting of di-isoamylamine, diethylbenzylamine, dimethylbenzylamine, and tri-isobutylamine.

38. A powder comprising microcapsule particles wherein the microcapsule particles have relatively uniform shape and narrow particle size distributions and wherein the microcapsule particles comprise: (a) a first polymer; (b) a second polymer, where the first and second polymers are uniformly dispersed, oppositely charged, held together by electrostatic forces, and form a polymer matrix; and (c) a cargo uniformly dispersed throughout the polymer matrix.

39. The powder of any preceding or following embodiment, where the powder is insoluble in an aqueous solution.

40. The powder of any preceding or following embodiment, wherein the polymer matrix of the powder is not crosslinked.

As used herein, the singular terms "a," "an," and "the" may include plural referents unless the context clearly dictates otherwise. Reference to an object in the singular is not intended to mean "one and only one" unless explicitly so stated, but rather "one or more."

As used herein, the term "set" refers to a collection of one or more objects. Thus, for example, a set of objects can include a single object or multiple objects.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, "substantially" aligned can refer to a range of angular variation of less than or equal to ±10°, such as less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

Additionally, amounts, ratios, and other numerical values may sometimes be presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Formulations used in the formation of CoCo particles by spray drying

| CoCo Formulation[1] | Feed pH adjusted using | pH of spray-drying feed | Final pH[2] | Powder yield (%) | Soluble in water?[3] | Extent of Complex Coacervation (%) |
|---|---|---|---|---|---|---|
| 1 | NaOH | 8.5 | 6.4 | 58.3 | Yes | 0 ± 0 |
| 2 | NH$_4$OH | 8.5 | 5.1 | 53.3 | Partial | 9 ± 2 |
| 3 | NH$_4$OH and succinic acid | 8.5 | 4.3 | 70.1 | No | 64 ± 6 |
| L-CoCo | NH$_4$OH and succinic acid | 8.5 | 4.3 | 61.8 | No | 75 ± 6 |

[1]All the formulations contained the same concentrations of gelatin and alginate.
[2]Final pH of the sample after spray-drying was determined by measuring the pH of the water into which the powders were suspended. Water alone had a pH of 6.
[3]Solubility by visual inspection after suspending in water.

TABLE 2

Volatile Retention of L-CoCo During Spray Drying and Storage

| Sample ID[1] | Emulsion size (um)[7] | Time in collection chamber (min) | Shelf storage (days) | In Feed (%, d.b.) | d-limonene content ± SD Powder surface (%, d.b.) | Spray-dried powder (%, d.b.) | Volatile retention[8] (%) |
|---|---|---|---|---|---|---|---|
| L-CoCo[2] | 15 | 12 | 0 | 20.4 ± 0.8 | 0.24 ± 0.0 | 16.9 ± 0.2 | 82.7 ± 3.6 |
| LT-L-CoCo[3] | 15 | 35 | 0 | 20.4 ± 0.8 | 0.22 ± 0.0 | 16.2 ± 0.1 | 79.4 ± 3.3 |
| LS-L-CoCo[4] | 15 | 12 | 72 | 20.4 ± 0.8 | 0.13 ± 0.0 | 16.3 ± 0.1 | 80.0 ± 3.3 |
| LTLS-L-CoCo[3,4] | 15 | 35 | 72 | 20.4 ± 0.8 | 0.11 ± 0.0 | 14.3 ± 0.2 | 69.9 ± 4.2 |
| LH-L-CoCo[5] | 69 | 12 | 0 | 20.2 ± 1.0 | 0.22 ± 0.0 | 14.6 ± 0.3 | 72.6 ± 3.8 |
| U-L-CoCo[6] | 6 | 12 | 0 | 19.4 ± 1.0 | 0.12 ± 0.0 | 8.3 ± 0.3 | 42.5 ± 2.0 |

[1]All samples use the same formulation as the L-CoCo (baseline) sample.
[2]L-CoCo sample was prepared by two-stage emulsification—coarse emulsion followed by high-pressure homogenization.
[3]LT: long time in collection chamber, where the outlet temperature was in the range of 87-92° C.
[4]LS: long term storage in sealed vial at room temperature;
[5]LH: low level of homogenization. LH-L-CoCo sample was prepared by two-stage emulsification—coarse emulsion followed by low level of homogenization.
[6]U-L-CoCo sample was prepared with coarse emulsion by Ultra-Turrax T-18.
[7]The volume-weighted mean diameter ($D_{4,3}$) of emulsion.
[8]Volatile retention during spray drying does not account for losses during preparation of the feed.

TABLE 3

Comparison-VR of Limonene in Complex Coacervates and CLAMS Microcapsules formed with Sigma Alginates

| | Complex Coacervation Microcapsules[1] | Calcium Crosslinked Alginate Microcapsules (CLAMs) | |
|---|---|---|---|
| | | Gelatin as surfactant[2] | Whey protein as surfactant[2] |
| Surface limonene content in dry powder, % | 0.72 ± 0.04 | 0.23 ± 0.00 | 0.00 |
| Total limonene content in dry powder, % | 6.88 ± 0.05 | 5.11 ± 0.15 | 9.52 ± 0.22 |
| Initial limonene content in inlet feed, % dry basis | 18.37 ± 2.34 | 20.51 ± 0.31 | 22.89 ± 2.64 |
| Volatile retention, % | 37.02 ± 4.71 | 24.54 ± 0.79 | 41.03 ± 4.84 |
| # of days between spray drying and extraction (Surface limonene and total limonene) | 5 | 5 | 2 |
| pH of 1% (w/v) dispersion | 4.76 | Not Measured | Not Measured |
| Powder Yield (%) | 69.9 | 40.8 | 50.0 |

[1]Formulation for complex coacervation microcapsules: 2.5% (w/w) gelatin, 1% (w/w) Sigma low viscosity alginate, 1% (w/w) succinic acid and limonene. The pH of the dispersion was adjusted to about pH 8.7 with ammonium hydroxide (NH$_4$OH).
[2]Formulation for gelatin CLAMs: 2% (w/w) Sigma low viscosity alginate, 1% (w/w) succinic acid, 0.5% (w/w) CaHPO$_4$, limonene, and gelatin as surfactant. The pH of the dispersion was adjusted to about pH 7 with ammonium hydroxide (NH$_4$OH).
[3]Formulation for whey protein CLAMs: 2% (w/w) Sigma low viscosity alginate, 1% (w/w) succinic acid, 0.5% (w/w) CaHPO$_4$, limonene, and whey protein as surfactant. The pH of the dispersion was adjusted to about pH 7 with ammonium hydroxide (NH$_4$OH).

What is claimed is:

1. A method of causing complex coacervation of polymer molecules, comprising:
   (a) providing a solution of a first ionic polymer, a second ionic polymer with an isoelectric point (pI$_2$) or acid dissociation constant (pKa$_2$) that is greater than the isoelectric point (pI$_1$) or acid dissociation constant (pKa$_1$) of the first ionic polymer and a volatile base; and
   (b) volatilizing the volatile base of the solution, thereby reducing the pH of the solution and changing the charge of the second ionic polymer initiating electrostatic interactions with the first ionic polymer through complex coacervation to form a capsule, fiber, or film.

2. The method of claim 1, further comprising:
adding a cargo material to the solution prior to volatilization of the volatile base.

3. The method of claim 1, further comprising:
controlling volatile base vaporization temperatures to control the rate of change of pH in the solution.

4. The method of claim 1, wherein said volatile base of said solution is ammonium hydroxide.

5. The method of claim 1, wherein said volatile base is selected from the group of volatile amine bases consisting of diethylamine, propylamine, isopropylamine, methylamine, dimethylamine and isobutylamine.

6. The method of claim 1, said solution further comprising:
a non-volatile acid to further lower the pH for enhancement of complex coacervation during spray drying depending on the selection of ionic polymers.

7. The method of claim 6, wherein said acid is an organic acid selected from the group of acids consisting of malic acid, tartaric acid, oxalic acid, adipic acid, glutaric acid, citric acid, succinic acid and ascorbic acid.

8. The method of claim 1, further comprising:
controlling a degree of complex coacervation by modulating one or more of the following: first and second ionic polymer concentrations, volatile or non-volatile acid concentration of the solution or volatile or non-volatile base concentration of the solution.

9. A method of causing complex coacervation of polymer molecules, comprising:
(a) providing a solution of a first ionic polymer, a second ionic polymer with an isoelectric point ($pI_2$) or acid dissociation constant ($pKa_2$) that is greater than the isoelectric point ($pI_1$) or acid dissociation constant ($pKa_1$) of the first ionic polymer and a volatile acid; and
(b) volatilizing the volatile acid of the solution, thereby increasing the pH of the solution and changing the charge of the first ionic polymer initiating electrostatic interactions with the second ionic polymer through complex coacervation to form a capsule, fiber, or film;
(c) wherein said volatile acid of the solution is selected from the group of volatile acids consisting of acetic acid, formic acid, and carbonic acid.

10. The method of claim 9, further comprising:
adding a cargo material to the solution prior to volatilization of the volatile acid.

11. The method of claim 9, further comprising:
controlling volatile acid vaporization temperatures to control the rate of change of pH in the solution.

12. The method of claim 9, said solution further comprising:
a non-volatile base to further increase the pH for enhancement of complex coacervation during spray drying depending on the selection of ionic polymers.

13. The method of claim 12, wherein said non-volatile base is an amine selected from the group of non-volatile amines consisting of di-isoamylamine, diethylbenzylamine, dimethylbenzylamine, and tri-isobutylamine.

14. The method of claim 9, said solution further comprising:
a non-volatile acid to further lower the pH for enhancement of complex coacervation during spray drying depending on the selection of ionic polymers.

15. A method of causing complex coacervation of polymer molecules, comprising:
(a) providing a solution of a first ionic polymer, a second ionic polymer with an isoelectric point ($pI_2$) or acid dissociation constant ($pKa_2$) that is greater than the isoelectric point ($pI_1$) or acid dissociation constant ($pKa_1$) of the first ionic polymer, a volatile acid and a non-volatile base; and
(b) volatilizing the volatile acid of the solution, thereby increasing the pH of the solution and changing the charge of the first ionic polymer initiating electrostatic interactions with the second ionic polymer through complex coacervation to form a capsule, fiber, or film.

16. The method of claim 15, wherein said non-volatile base is an amine is selected from the group of non-volatile amines consisting of di-isoamylamine, diethylbenzylamine, dimethylbenzylamine, and tri-isobutylamine.

17. The method of claim 15, wherein said volatile acid of the solution is selected from the group of volatile acids consisting of acetic acid, formic acid, and carbonic acid.

* * * * *